United States Patent [19]
Knippscheer et al.

[11] Patent Number: 5,171,527
[45] Date of Patent: Dec. 15, 1992

[54] APPARATUS FOR REMOVING FLUID FROM AN UMBILICAL CORD

[75] Inventors: Hermann Knippscheer, Baldwin, N.Y.; Daniel D. Richard, Sedona, Ariz.

[73] Assignee: Cryo-Cell International, Inc., Baldwin, N.Y.

[21] Appl. No.: 537,418

[22] Filed: Jun. 13, 1990

Related U.S. Application Data
[63] Continuation-in-part of Ser. No. 471,084, Jan. 26, 1990.

[51] Int. Cl.⁵ ..................... G01N 35/06; G01N 21/00
[52] U.S. Cl. .................... 422/50; 422/82.05; 422/63; 422/105; 422/108; 73/863.01; 73/864.23; 73/864.25
[58] Field of Search ............... 422/63, 64, 106, 108, 422/100, 99, 82.05, 50, 105; 436/49, 54; 604/119, 317; 141/65, 95, 130; 73/863.01, 863.85, 864.23, 864.24, 864.25

[56] References Cited

U.S. PATENT DOCUMENTS

| | | | |
|---|---|---|---|
| 3,748,911 | 7/1973 | Rousselet et al. | 73/864.25 |
| 4,794,085 | 12/1988 | Jessop et al. | 436/54 |
| 4,818,492 | 4/1989 | Shimizu | 422/100 |
| 4,962,041 | 10/1990 | Roginski | 436/150 |
| 5,012,845 | 5/1991 | Averette | 141/329 |

Primary Examiner—Robert J. Warden
Assistant Examiner—T. A. Trembley
Attorney, Agent, or Firm—R. Neil Sudol; Henry D. Coleman

[57] ABSTRACT

A system for preparing a flexible elongate fluid-containing member for storage comprises a transparent perforated hollow shaft for supporting the fluid-containing member in a coiled configuration and a cup-shaped cleaning device for automatically dispensing a cleaning fluid onto the fluid-containing member while it is held in the coiled configuration on the support shaft. A transfer mechanism is provided for automatically transferring the fluid-containing member in the coiled configuration from the support shaft to a receptacle, and an aspirator is provided for automatically removing liquid from the fluid-containing member prior to transference thereof from the support shaft to the receptacle. The receptacle includes a central finger defining with an outer wall an annular storage chamber for maintaining the elongate member in a coiled configuration during storage.

7 Claims, 9 Drawing Sheets

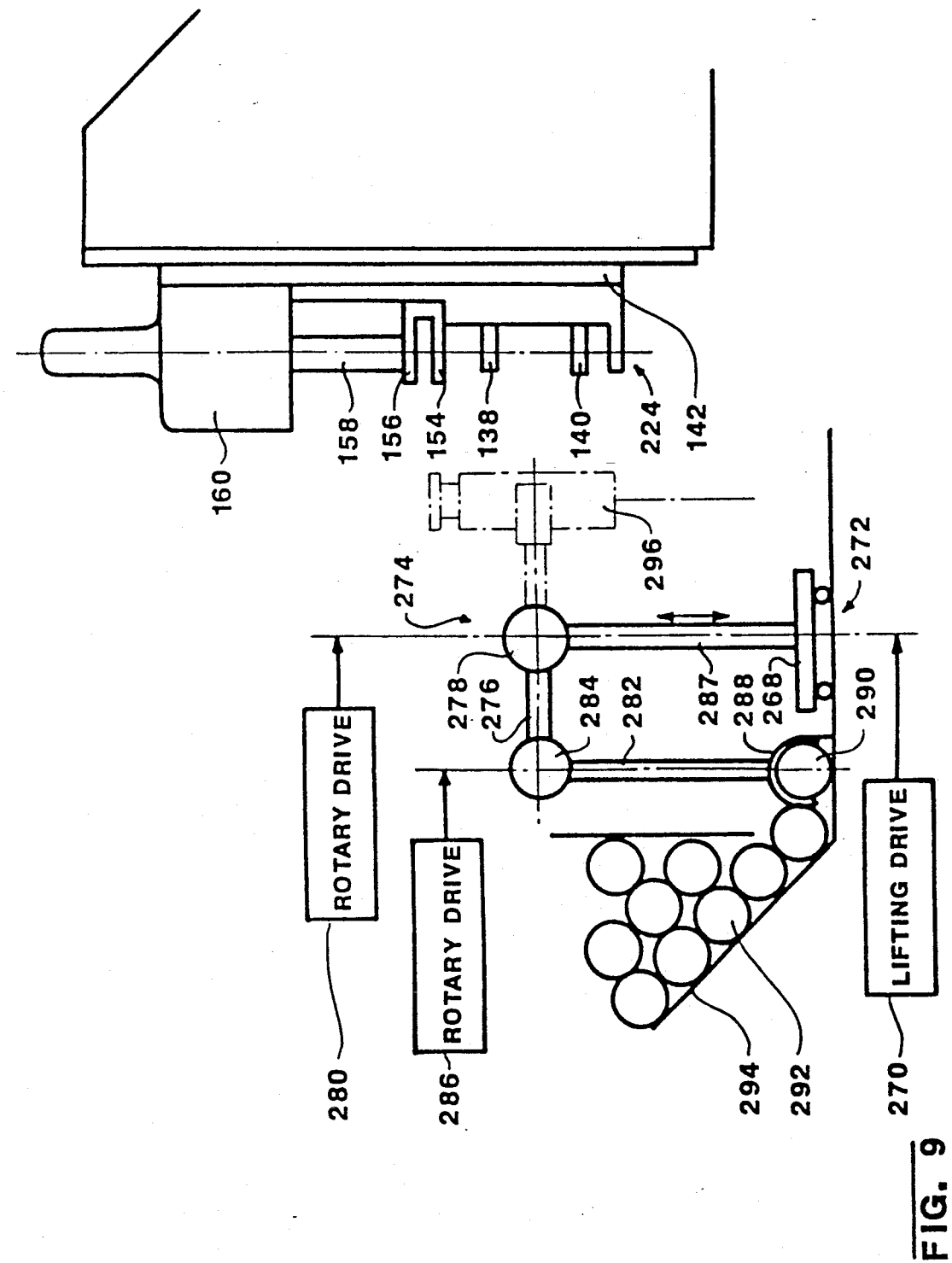

APPARATUS FOR REMOVING FLUID FROM AN UMBILICAL CORD

CROSS-REFERENCE TO A RELATED APPLICATION

This application is a continuation-in-part of commonly owned U.S. patent application Ser. No. 471,084 filed Jan. 26, 1990.

BACKGROUND OF THE INVENTION

This invention relates to an apparatus for loading a flexible elongate member into a vial. This invention also relates to an apparatus for cleaning the elongate member and to an apparatus for aspirating a quantity of fluid from the elongate member, prior to loading the member into the vial.

This invention additionally relates to a combination system including an apparatus for cleaning the elongate member, an apparatus for aspirating a quantity of fluid from the elongate member, and an apparatus for loading a flexible elongate member into a vial.

This invention relates further to a specialized vial for holding a coiled elongate member.

The invention is particularly adapted to preparing an umbilical cord for storage, as described in commonly owned U.S. patent application Ser. No. 455,170 filed Dec. 22, 1989, the disclosure of which is hereby incorporated by reference.

As discussed in U.S. patent application Ser. No. 455,170, umbilical cords from infants born within a prescribed territory (a city, county, state or an entire country) are sectioned, preserved and stored. Also stored is information pertaining to each individual such as the infant's name, birth statistics and any pertinent information as to genetic predisposition to certain diseases. That information may be stored in a computer for subsequent use.

As further discussed in U.S. patent application Ser. No. 455,170, the preserved umbilical cords or portions thereof are subsequently made available for medical identification, research purposes or therapeutic treatment upon proper request. The DNA contents of the umbilical cord is useful for medical identification, while the cellular contents of the cord are useful for therapeutic treatment. More particularly, in accordance with the disclosure of application Ser. No. 455,170, the stem cells in the blood contained in the veins and artery of the cord may be used in hematopoietic reconstitution of leukemic patients. For such purposes, it is desirable that umbilical cords be stored for periods of greater or lesser duration and that the umbilical cords be marked or banded for identification.

OBJECTS OF THE INVENTION

An object of the present invention is to provide an apparatus for automatically loading a flexible elongate fluid-containing member into a storage receptacle.

Another object of the present invention is to provide a storage receptacle which serves to maintain a flexible elongate fluid-containing member in a coiled storage configuration.

Another, more particular, object of the present invention is to provide such a receptacle which optimizes heat transfer to and from the stored elongate fluid-containing member.

Yet a further object of the present invention is to provide an apparatus for automatically cleaning a flexible elongate member prior to insertion thereof in a coiled configuration inside a storage vial.

An additional object of the present invention is to provide an apparatus for automatically removing a quantity of fluid from a flexible elongate fluid-containing member prior to insertion thereof in a coiled configuration inside a storage vial. If the fluid-containing member is an umbilical cord, the present invention intended to enable removal of a quantity of blood from an umbilical cord vein or artery.

Yet another object of the present invention is to provide a method for identifying elongate fluid-containing members such as umbilical cords which are subjected to storage.

SUMMARY OF THE INVENTION

A storage vial in accordance with the present invention comprises an outer wall having a longitudinal axis and an inner wall substantially coaxial with the outer wall and spaced therefrom to form therewith a substantially annular holding chamber. The vial further comprises a substantially annular base wall at one end of the container, the base wall connecting the inner wall and the outer wall to one another. A lid is releasably attached to the container at at end thereof opposite the base wall.

Preferably, the outer wall and the inner wall are both cylindrical, while the base wall has an arcuate transverse cross-section. It is also preferred that the inner wall is hollow and is provided with an opening at the base wall. The hollow inner wall receives a finger of a transfer mechanism and also serves to increase the surface area of the vial available for heat exchange. A coolant material such as vaporous or liquid nitrogen is able to penetrate into the space defined by the inner wall and thereby substantially increase the rate of heat transfer from the vial.

Pursuant to another feature of the present invention, the lid is provided with a projection fitting into a recess defined by the inner wall at an end thereof opposite the base wall. The lid is provided with a magnetizable element such as a metal insert disposed in part in the projection, whereby the vial may be automatically moved by a conveyance mechanism with a magnetic holding device.

A vial in accordance with the present invention is particularly well adapted for cryogenically storing flexible elongate members such as umbilical cords. The annular holding chamber of the vial maintains the umbilical cord in a spiraling or coiled configuration, reduces the amount of air inside the vial, which promotes heat transfer, and maximizes the surface area through which heat exchange occurs. In addition, the maintenance of the umbilical cord in the spiraling or coiled configuration ensures as nearly as possible an even rate of heat transfer along the length of the cord.

An apparatus for cleaning a flexible elongate member such as an umbilical cord comprises, in accordance with the present invention, a holder for releasably maintaining the flexible elongate member in a coiled configuration, a cup-shaped member removably positionable about the flexible elongate member while that member is maintained in the coiled configuration by the holder, and a dispenser for spraying or otherwise ejecting a cleaning fluid from an inner surface of the cup-shaped member.

Pursuant to another feature of the present invention, the holder includes a shaft and a support for supporting the shaft in a predetermined orientation. The shaft is preferably hollow and is permeable to the cleaning fluid. Accordingly, the cup-shaped member is provided with a finger insertable into the shaft during a positioning of an annular wall of the cup-shaped member about the shaft.

Pursuant to another feature of the present invention, the fluid dispenser includes (a) perforations in the inner surface of the cup-shaped member and the finger, (b) a source of the cleaning fluid and (c) a conduit in the cup-shaped member for guiding the cleaning fluid from the source to the perforations.

Pursuant to a specific feature of the present invention, the holder further includes a clamping element on the shaft, whereby the elongate member is releasably attached to the shaft. The clamping member is advantageously slidably attached to the shaft.

Pursuant to another specific feature of the present invention, a rotary drive is operatively connected to the shaft. The rotary drive facilitates disposition of the flexible elongate member in a coiled configuration about the shaft and enhances the cleaning process by turning the shaft about a longitudinal axis during a fluid-dispensing operation.

Pursuant to yet another specific feature of the present invention, the cleaning apparatus further comprises a guide particularly in the form of a hood member slidably mounted to the rotary drive for guiding the cleaning fluid, upon a dispensing of the cleaning fluid from the inner surface of the cup-shaped member, away from a chamber formed thereby.

The cleaning apparatus advantageously includes means for moving air over the flexible elongate member upon cleaning thereof by the cleaning fluid.

An apparatus for removing a sample of fluid from a fluid-containing member having an external membrane comprises, in accordance with the present invention, a holder for supporting the fluid-containing member in a coiled configuration and an aspirator for puncturing the membrane of the fluid-containing member and aspirating a quantity of fluid from the fluid-containing member while the fluid containing member is supported in the coiled configuration by the holder.

Pursuant to another feature of the present invention, the apparatus for removing fluid from the fluid-containing member further comprises a detector or sensor for detecting a location of fluid within the fluid-containing member. A carriage is provided for moving one of the holder and the aspirator relative to the other. And a control unit is operatively connected to the detector and the carriage for controlling the motion of the holder and the aspirator relative to one another. The control unit is also operatively connected to the aspirator for triggering the operation thereof upon an attainment of a desired relative position of the holder and aspirator.

Pursuant to a further feature of the present invention, the holder includes a shaft, a support for supporting the shaft in a predetermined orientation, and a clamp element for releasably holding the fluid-containing member in a coiled configuration about the shaft.

Pursuant to a particular feature of the present invention, the shaft is at least partially hollow and the detector includes a light source and a photodetector for sensing an internal structure of the fluid-containing member. More particularly, the detector further includes a first drive for shifting the light source into the shaft and a second drive for rotating the photodetector in an arc about a coil of the fluid-containing member.

An apparatus for loading a flexible elongate member into a receptacle comprises, in accordance with the present invention, a holder for releasably holding the fluid-containing member in a coiled configuration, a support for supporting the receptacle in a predetermined orientation relative to the holder, and a deposition device for moving the flexible elongate member from the holder into the receptacle.

Pursuant to another feature of the present invention, a drive is operatively connected to at least one of the holder and the support for moving the holder and the support relative to one another to insert the flexible elongate member into the receptacle. A retainer member is provided for engaging the coiled flexible elongate member and shifting the coiled flexible elongate member from the holder into the receptacle.

A system for preparing a flexible elongate fluid-containing member for storage comprises, in accordance with the present invention, a support for supporting the fluid-containing member in a coiled configuration and a removal device for automatically transferring the fluid-containing member in the coiled configuration from the support to a receptacle.

In another embodiment, the system also comprises a cleaning device for automatically dispensing a cleaning fluid onto the fluid-containing member while same is held in the coiled configuration on the support.

As described hereinabove, the cleaning device may specifically include a cup-shaped member removably positionable about the fluid-containing member while the latter is maintained in the coiled configuration by the support. A fluid dispenser is provided for dispensing a cleaning fluid from an inner surface of the cup-shaped member.

As also described above, the support preferably includes a rotatable hollow shaft permeable to the cleaning fluid, while the cup-shaped member is provided with a finger insertable into the shaft during a positioning of an annular wall of the cup-shaped member about the shaft. More specifically, the fluid dispenser includes (a) perforations in the inner surface of the cup-shaped member and the finger, (b) a source of the cleaning fluid and (c) a conduit in the cup-shaped member for guiding the cleaning fluid from the source to the perforations.

As additionally described above, the cleaning device of the system advantageously includes a guide for channeling the cleaning fluid, upon a dispensing thereof from the inner surface of the cup-shaped member, away from a chamber formed by the cup-shaped member. The guide takes the form of a hood member removably positionable about an open end of the cup-shaped member, the hood member being provided with an opening traversable by the cup-shaped member. The cleaning device also includes means for moving air over the flexible elongate member upon cleaning thereof by the cleaning fluid.

In another embodiment of the system, the system further comprises a fluid removal device for automatically removing liquid from the fluid-containing member prior to transference thereof from the support to the receptacle. Specifically, the removal device takes the form of an aspirator and includes (a) a detector for locating liquid within the fluid-containing member, (b) a carriage for moving one of the support and the aspirator relative to the other, and (c) a control unit operatively connected to the detector and the carriage for controlling the motion of the support and the aspirator relative to one another, the control unit being operatively connected to the aspirator for triggering the operation thereof upon an attainment of a desired relative position of the support and aspirator.

Pursuant to another feature of the present invention, as discussed above, the support includes a shaft and a clamp or other element for releasably holding the fluid-containing member in a coiled configuration about the shaft. Preferably, the shaft is at least partially hollow and the detector includes a light source and a photodetector for sensing an internal structure of the fluid-containing member. The detector further includes a drive for shifting the light source into the shaft.

BRIEF DESCRIPTION OF THE DRAWING

FIG. 9 is a partially schematic side elevational view of a syringe loading apparatus in accordance with the present invention.

DETAILED DESCRIPTION OF THE INVENTION

Figure 1:
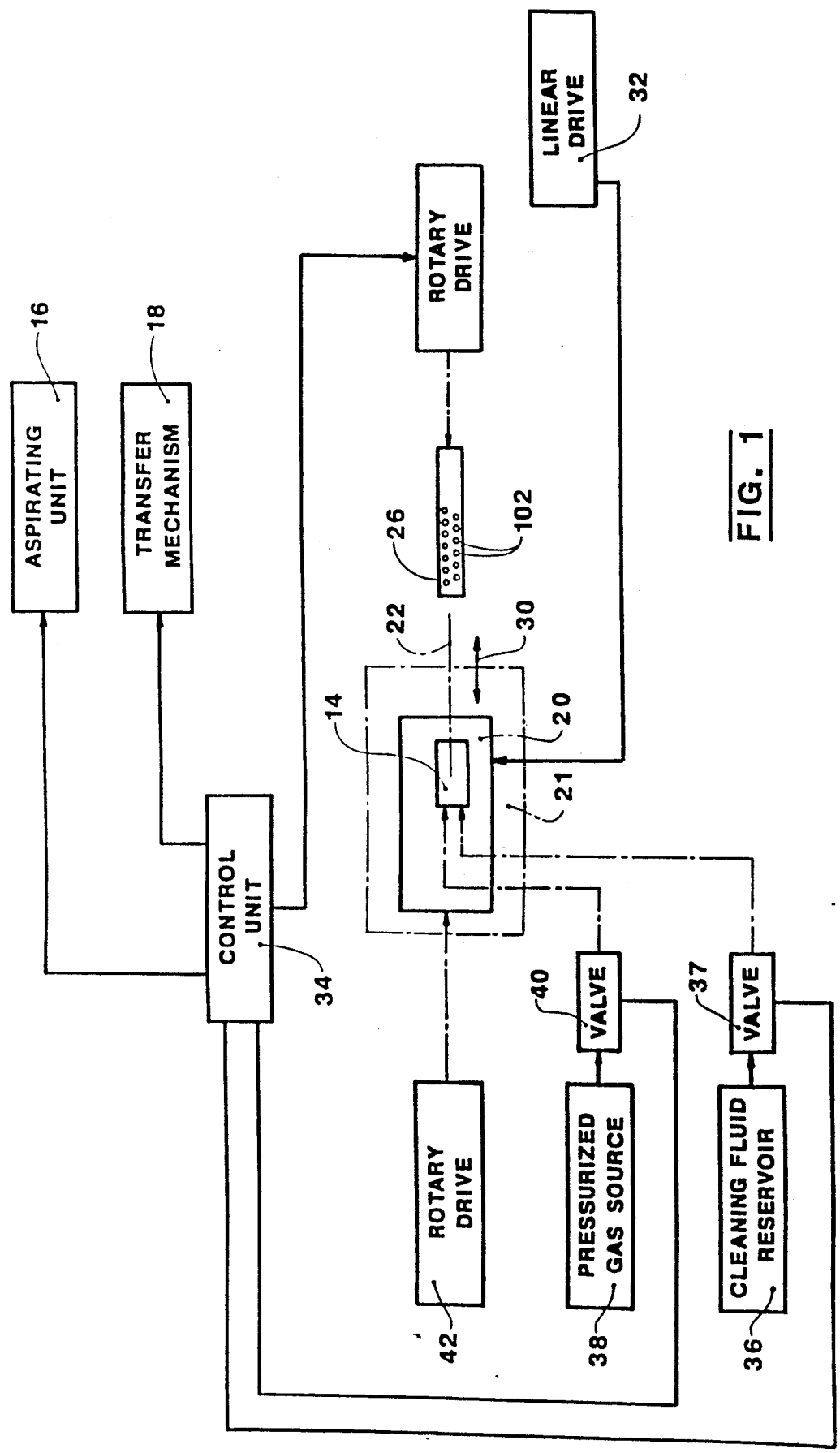
FIG. 1 is a schematic block diagram of a system for cleaning and aspirating fluid from a flexible elongate member and for loading the member into a vial, in accordance with the present invention.

As illustrated schematically in FIG. 1, a system for preparing a flexible elongate fluid-containing member 12 such as an umbilical cord (see FIG. 2) for storage comprises a cleaning unit 14, an aspirating unit 16 and a transfer mechanism 18 all mounted to a carousel 20 for rotation about a horizontal axis 22. As described in detail hereinafter, aspirating unit 16 functions to withdraw an aliquot of liquid from umbilical cord 12, for example, blood from a vein or artery thereof. Transfer mechanism 18 serves to slide the umbilical cord 12 into a receptacle or vial 24 (see FIG. 2) from a hollow shaft 26 about which the cord is wound in a coiled configuration.

Cleaning unit 14 includes a cup-shaped member 28 (FIG. 3) mounted to a face of carousel 20 which is itself shiftably mounted to a frame 21 for executing a reciprocating type motion, as indicated by arrow 30. Carousel 20 is moved by a linear drive 32 in response to signals generated by a control unit 34. Cup-shaped cleaning device 28 communicates with a reservoir 36 of cleaning fluid such as an antibacterial aqueous solution via a first valve 37 and with a source 38 of pressurized air via a second valve 40, both valves being actuated by control unit 34. The structure and operation of cup-shaped cleaning device 28 is described in greater detail hereinafter with reference to FIG. 3.

As further illustrated in FIG. 1, the system also includes a rotary drive 42 operatively coupled with carousel 20 for intermittently rotating that superstructure component relative to frame 21 to place cleaning unit 14, aspirating unit 16 and transfer mechanism 18 alternately in juxtaposition to a free end of shaft 26. Upon the completion of such a juxtaposition, control unit operates linear drive 32 to move the respective unit into an operative position relative to shaft 26.

Figure 2:
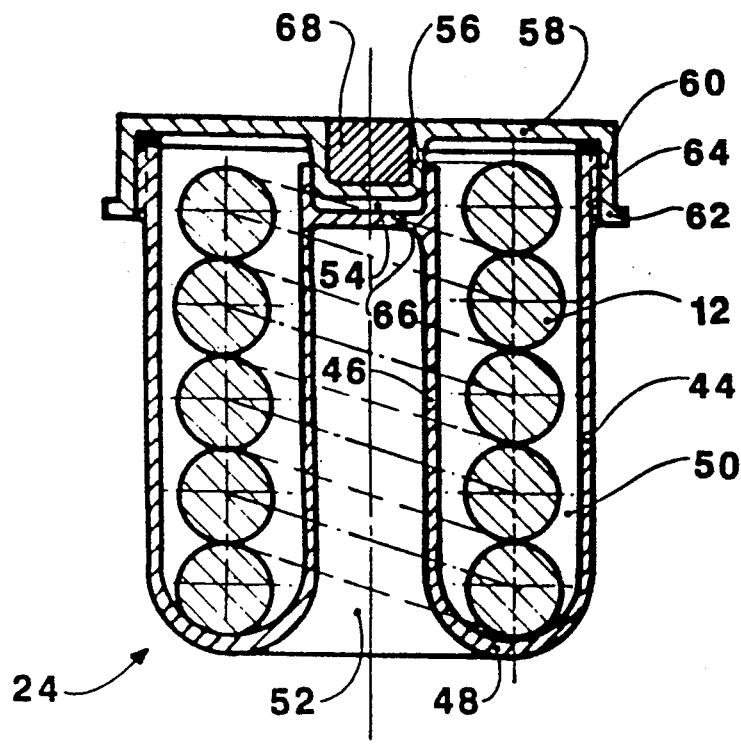
FIG. 2 is a cross-sectional view of a vial or storage receptacle in accordance with the present invention.

As depicted in FIG. 2, vial 24 comprises a cylindrical outer wall 44, a cylindrical inner wall 46 coaxial therewith and an annular base wall 48 at a bottom end of the vial. Base wall 48 has an arcuate, upwardly concave cross-section and connects inner wall 46 to outer wall 44. Outer wall 44 and inner wall 46 define an annular holding chamber 50 in which umbilical cord 12 is deposited in a spiral or coiled configuration as described in detail below.

Inner wall 46 takes the form of a central finger provided at a bottom end, i.e., in a plane defined by base wall 48, an opening or mouth 52. At an opposite end, inner wall 46 defines a recess 54 which receives a projection or plug 56 on an inner side of a receptacle cap or lid 58. Cap 58 is provided with a longitudinally extending peripheral flange 60 in turn provided along a free edge or rim with an outwardly turned rib or bead 62. Flange 60 is provided along a cylindrical inner surface with a screw thread 64 mating with a similarly formed screw thread on outer wall 44. Inner wall 46 is provided on an inner surface with a transversely extending reinforcement wall 66.

A magnetizable element or metal insert 68 is mounted in plug portion 56 of cap 58. Magnetizable element 68 enables automatic transfer of vial 24 by a magnetic conveyance device such as that disclosed in commonly owned U.S. patent application Ser. No. 389,543 filed Aug. 4, 1989, the disclosure of which is hereby incorporated by reference herein. In addition, annular rib 62 enables vial 24 to rest on a conveyor bar provided with apertures as further disclosed in that application.

Figure 3:
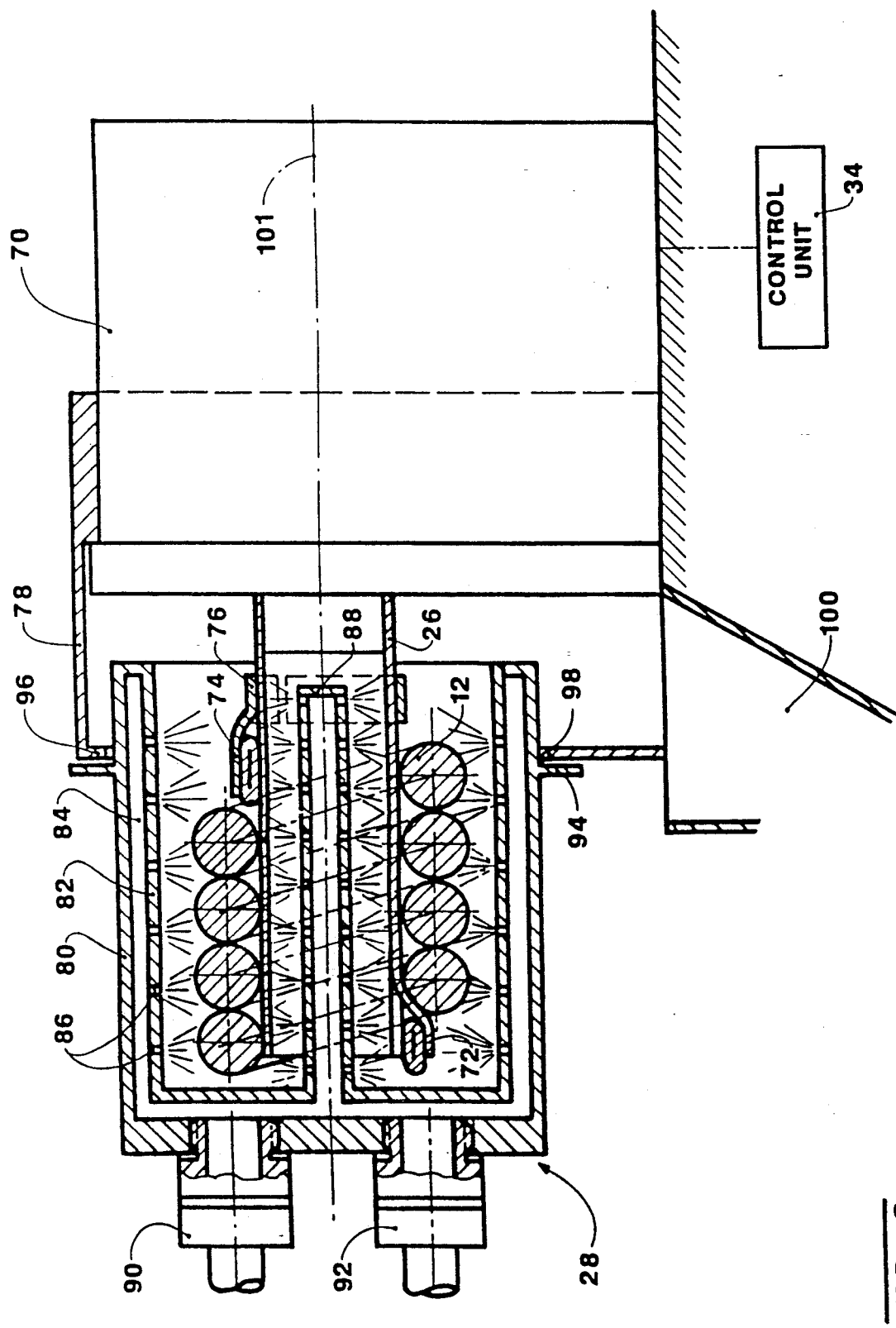
FIG. 3 is partially a cross-sectional view and partially a side elevational view of a cleaning apparatus indicated schematically in FIG. 1.

As shown in FIG. 3, umbilical cord 12 is wound in a coiled configuration about support shaft 26. Shaft 26 is mounted to the rotor 71 (see FIG. 5) of a rotary drive motor 70 operatively linked to control unit 34. Prior to winding about shaft 26, the ends of umbilical cord 12 are preferably closed off, for example, by strings or staples (not shown). Umbilical cord 12 is held to shaft 26 by a pair of spring clamps 72 and 74. Clamp 72 is fixed to a free end of shaft 26, while clamp 74 is mounted to a collar 76 in turn slidably secured to shaft 26 proximately to drive motor 70. In attaching umbilical cord 12 to shaft 26, an operator inserts one end of the cord between clamp 72 and shaft 26. Motor 70 is then energized to implement a cord winding operation. Clamp 74 is then manually slid into position over the other end of umbilical cord 12.

To clean umbilical cord 12, control unit 34 rotates carousel 20 (FIG. 1) so that cup-shaped cleaning device 28 is aligned with shaft 26. Drive 32 is then activated by control unit 34 to shift cup-shaped cleaning device 28 over shaft 26 and umbilical cord 12 wound thereon. A hood 78 slidably mounted to motor 70 is subsequently slid into an extended functional position (FIG. 3) from a retracted rest position (FIG. 6) over motor 70. The shifting of hood 78 may be accomplished manually by an operator or automatically under the action of control unit 34.

As depicted in detail in FIG. 3, cup-shaped cleaning device 28 includes a cylindrical cup-shaped outer wall 80 spaced from a cup-shaped inner wall 82 to form a cup-shaped conduit or chamber 84 for distributing cleaning fluid to a multiplicity of perforations 86 provided in inner wall or surface 82. Extending from inner wall 82 coaxially therewith is an integral hollow finger or central projection 88 also formed with perforations 86 communicating with conduit 84. Outer wall 80 of cup-shaped cleaning device 28 is provided with a pair of fittings 90 and 92 coupled to valves 37 and 40 (FIG. 1) for receiving cleaning fluid and pressurized gas or air from reservoir 36 and source 38, respectively. Outer wall 80 is additionally provided with a radially extending circumferential flange 94 which cooperates with a lip 96 about an opening 98 in hood 78 to form an annular labyrinthine seal to prevent cleaning fluid from escaping cup-shaped cleaning device 28 except through hood 78. Hood 78 serves therefore to guide effluent cleaning fluid from cup-shaped cleaning device 28 into a run-off disposal funnel 100.

Upon a shifting of cup-shaped cleaning device 28 over shaft 26 and umbilical cord 12 wound thereon and upon a placing of hood 78 into its operative fluid-guiding position, motor 70 is energized to rotate shaft 26 about its longitudinal axis 101. In addition, valve 37 is opened to thereby introduce cleaning fluid into conduit 84 and to dispense the cleaning fluid therefrom through nozzles or perforations 86. Shaft 26 is permeable to liquid, to permit the cleaning of umbilical cord 12 by cleaning fluid dispensed or sprayed from finger 88 through perforations 86. Shaft 26 is preferably made of a transparent rigid polymeric material provided with an array of apertures 102 (FIG. 1). Alternatively, shaft 26 may be fabricated from a strong screen-like material.

Upon the lapse of a predetermined period, control unit 34 closes valve 37 and opens valve 40, thereby allowing air to flow through conduit 84 and perforations 86 into the space defined by cup-shaped cleaning device 28. The air dries umbilical cord 12.

Upon the completion of the drying operation, control unit 34 closes valve 40 and energizes drive 32 to remove cup-shaped cleaning device 28 from its operative position surrounding wound umbilical cord 12 into a neutral position. Hood 78 is also manually or automatically withdrawn back over motor 70.

Figure 4:
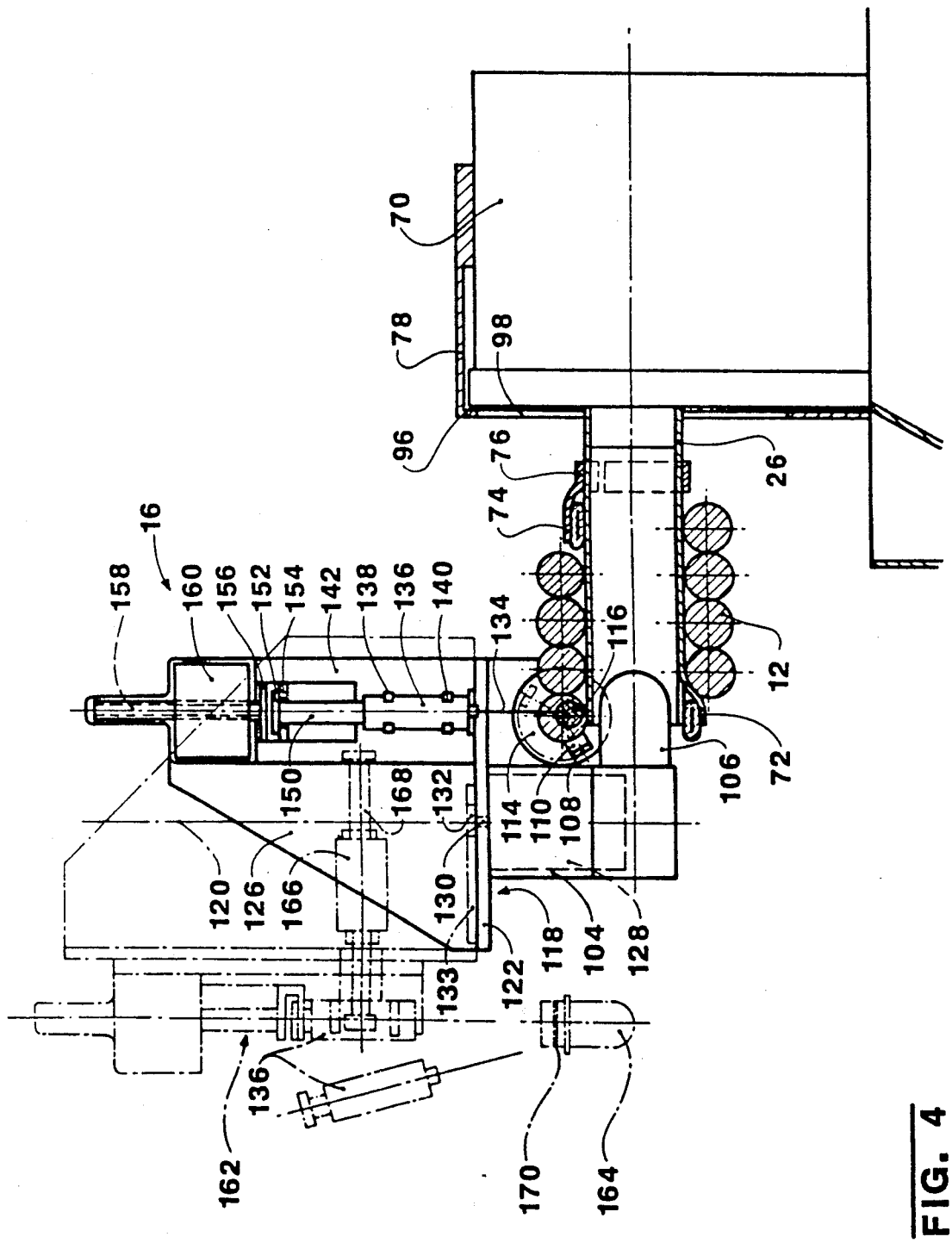
FIG. 4 is partially a cross-sectional view and partially a side elevational view of an aspirating unit shown schematically in FIG. 1.
Figure 5:
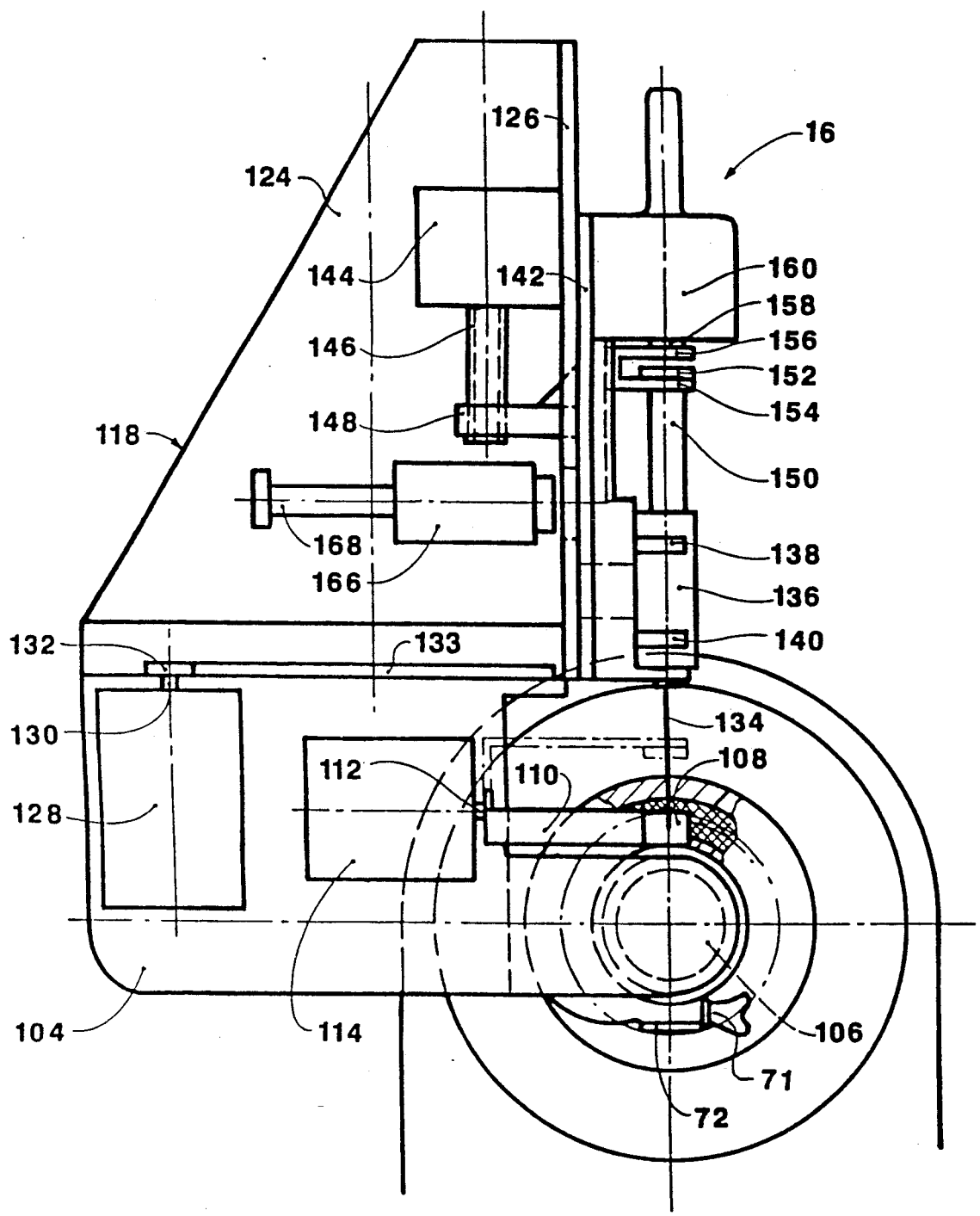
FIG. 5 is a front elevational view of the aspirating unit of FIG. 4.

As illustrated in detail in FIGS. 4 and 5, aspirating unit 16 comprises a primary frame 104 fixed to carousel 20 (FIG. 1). Attached to primary frame 104 is a light source bulb 106 which is inserted into shaft 26 at the free end thereof (FIG. 4) upon a rotation of carousel 20 so that aspirating unit 16 is aligned with the umbilical cord support shaft and upon a shifting of carousel 20 axially towards shaft 26. Light source 106 illuminates a coil of umbilical cord 12 at the free end of shaft 26, the radiant energy from source 106 entering the coil of umbilical cord 12 through the transparent material of shaft 26.

Aspirating unit 16 further comprises a photosensor 108 mounted to the free end of an L-shaped arm 110 in turn coupled to an output shaft 112 of a rotary drive 114 mounted to primary frame 104. Under the control of unit 34 (FIG. 1), rotary drive 114 pivots L-shaped arm 110 and photosensor 108 from an initial position approximately 30° below horizontal to an end position approximately 30° beyond vertical (dot-dash lines). During the pivoting of L-shaped arm 110 and photosensor 108 through approximately 150°, control unit 34 monitors output signals of the photosensor and calculates in response to those signals x-axis (horizontal, along shaft 26) and z-axis (vertical) coordinates of a vein or artery 116 inside umbilical cord 12. The outer membrane of umbilical cord 12 is sufficiently translucent to render possible such a photodetection process.

Aspirating unit 16 additionally comprises a secondary frame 118 rotatably mounted to primary frame 104 for limited pivoting motion about a vertical axis 120. Secondary frame 118 includes a base plate 122 and a pair of other plates 124 and 126 attached to base plate 122 and oriented orthogonally with respect to one another. The rotation of secondary frame 118 with respect to primary frame 104 is achieved by a motor 128 fastened to frame 104. Motor 128 has an output shaft 130 with a pinion 132 meshing with a large gear 133 connected to base plate 122. Motor 128 is energized by control unit 34 to shift a needle 134 of a hypodermic-type syringe 136 to the calculated x-axis position of vein or artery 116.

Syringe 136 is mounted via a pair of C-shaped spring clips 138 and 140 to a tertiary frame 142 slidably mounted to secondary frame 118 for linear motion in a vertical direction relative to the secondary frame. The vertical position of tertiary frame 142 is adjusted by a motor 144 mounted to plate 126 of secondary frame 118. Motor 144 has a threaded output shaft 146 meshing with an internally threaded bore (not designated) in a bracket member 148 rigid with tertiary frame 142.

At the onset of an aspirating operation, tertiary frame 142 and consequently hypodermic-type syringe 136 are disposed in a raised position wherein the tip of needle 134 is vertically spaced from umbilical cord 12. In addition, a plunger 150 of hypodermic-type syringe 136 is disposed in an inserted position. A flange 152 at the free end of plunger 150 is inserted between a first slotted plate 154 and a second plate 156 attached to the free end of a longitudinally shiftable output shaft 158 of a motor 160 which is fixed to tertiary frame 142 and which operates in response to output signals of control unit 34.

Upon completion of the x-axis positioning of needle 134 along the axis of shaft 26, control unit 34 transmits an energizing or enabling signal to motor 144 to cause the lowering of hypodermic-type syringe 136 from the raised position to a lowered position, shown in FIG. 4, wherein the tip of needle 134 is inserted into vein or artery 116. Upon the lowering of tertiary frame 142 and hypodermic-type syringe 136 the calculated distance, control unit 34 de-energizes motor 144 and activates motor 160 to withdraw plunger 150 from syringe 136, whereby blood fluid is suctioned from the interior of vein or artery 116.

Upon the completion of the aspirating operation, control unit 34 de-energizes motor 160 energizes motor 144 to lift tertiary frame 142 and thereby remove needle 144 from umbilical cord 12 and generates a signal inducing motor 128 to rotate secondary frame 118 90° about axis 120 to an ejection position 162 illustrated in dot-dash lines in FIG. 4. In ejection position 162, needle 134 is aligned with an ampule 164. Control unit 34 subsequently energizes motor 144 to lower tertiary frame 142 and hypodermic-type syringe 136 so that the tip of needle 134 is located within ampule 164. Motor 160 is then energized to push plunger 150 back into syringe 136 and thereby eject the aspirated cord blood into ampule 164. Upon the completion of the blood ejection, motor 160 is de-energized, while motor 144 is operated in a reverse direction to again raise tertiary frame 142 and hypodermic-type syringe 136. After tertiary frame 142 has been elevated to its raised position, control unit 34 operates a pneumatic or hydraulic cylinder 166 to shift a plunger member 168 to push hypodermic-type syringe 136 from its position within C-shaped spring clips 138 and 142. Syringe 136 is then discarded and another syringe is placed in clips 138 and 140 in preparation for a subsequent aspirating operation.

It is to be noted that the ejection of the cord blood from hypodermic-type syringe 136 need not be implemented in a vertical orientation as illustrated in FIG. 4. Instead, carousel 20 may be rotated to replace aspirating unit 16 with transfer mechanism 18 at the free end of shaft 26. Thus, while transfer mechanism 18 is operating to remove umbilical cord 12 from shaft 26, aspirating unit 16 may be operating to deposit the aspirated cord blood within ampule 164. Ampule 164 may in that case be provided at a mouth end with a membrane 170 which can be pierced by needle 134 but seals off the ampule upon the withdrawal of the needle during a return stroke of plunger 150.

Figure 6:
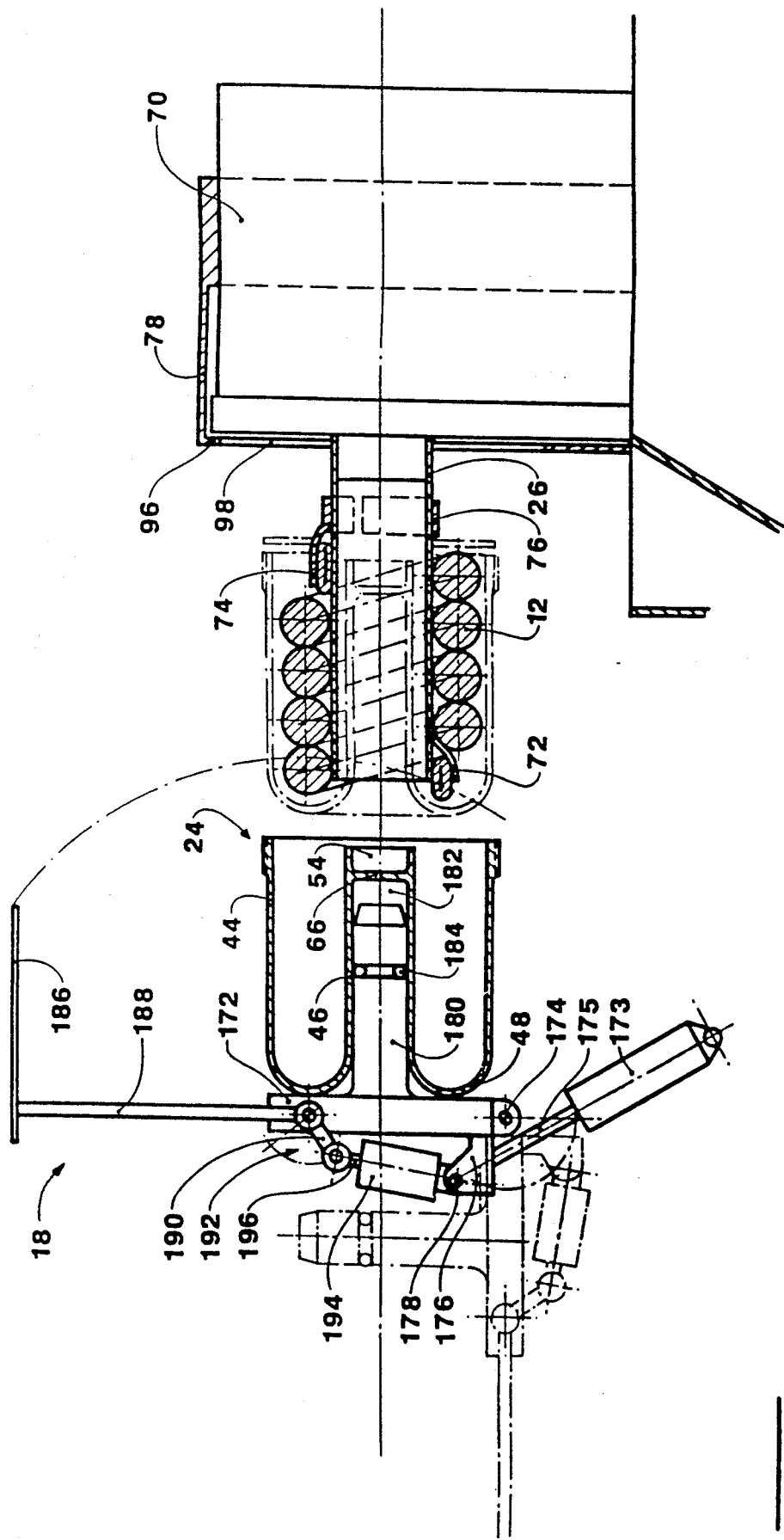
FIG. 6 is partially a cross-sectional view and partially a side elevational view of a transfer mechanism shown schematically in FIG. 1.

As illustrated in FIG. 6, transfer mechanism 18 includes a support plate 172 rotatably mounted to a face of carousel 20 for pivoting 90° about an axis 174 oriented perpendicularly with respect to the carousel face. The pivoting of support plate 172 is implemented by a pneumatic or hydraulic cylinder 173 having a plunger member 175 swingably fixed to a bracket 176 at a point 178.

Support plate 172 is provided on one side with a holding finger 180 inserted through opening or mouth 52 into an cylindrical space 182 defined by inner wall 46. Finger 180 is provided with a rubber O-ring 184 for increasing the frictional hold of the finger on vial 24. The outer cylindrical surface of finger 180 and the inner cylindrical surface of vial inner wall 46 are provided with interdigitating axially extending teeth (not shown) to prevent vial 24 from rotating with respect to finger 180 during a cap or lid screwing operation.

Figure 7:
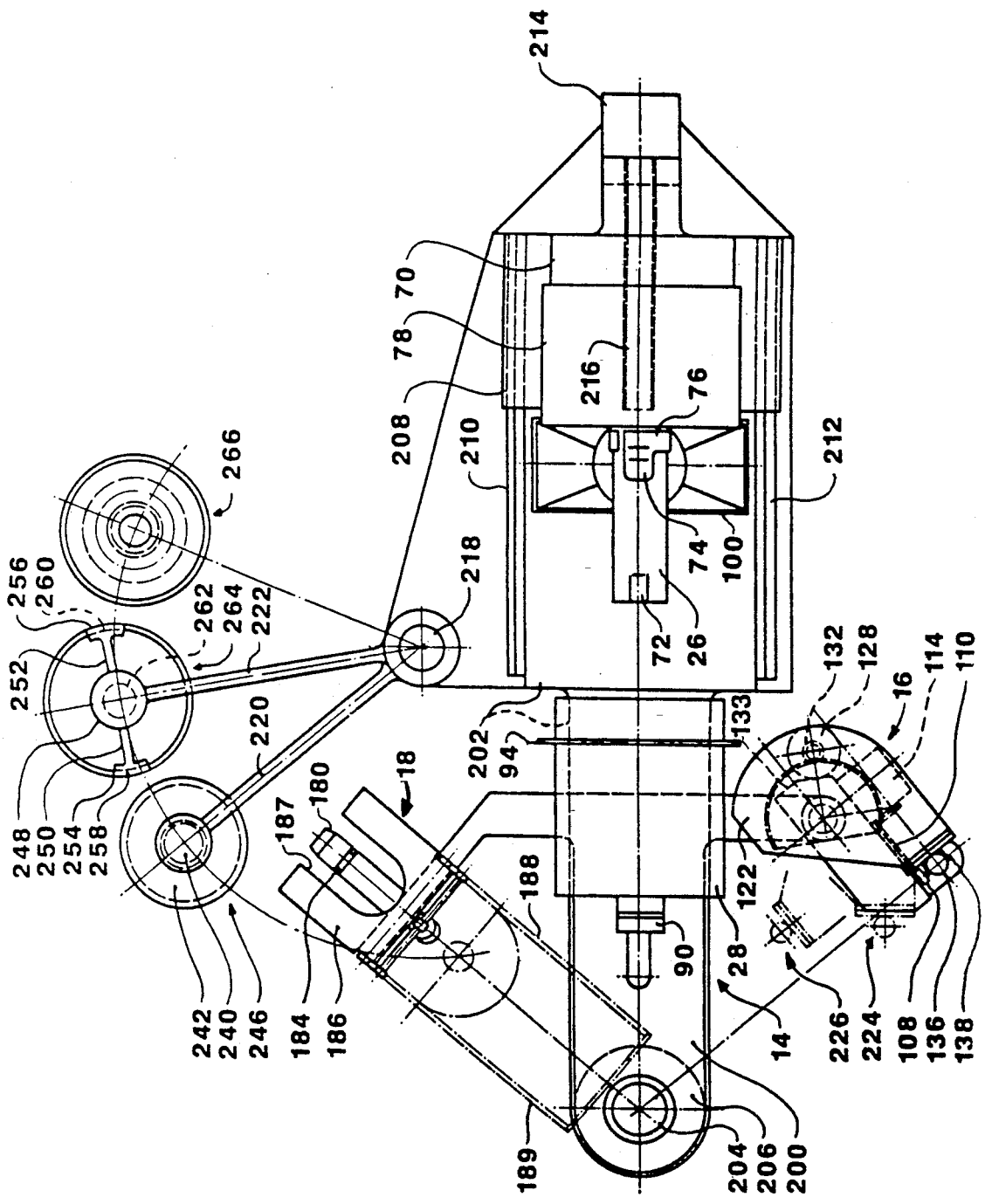
FIG. 7 is a top view of a system in accordance with the present invention, including the cleaning apparatus of FIG. 3, the aspirating unit of FIGS. 4 and 5 and the transfer mechanism of FIG. 6.

Transfer mechanism 18 further includes a retainer plate 186 pivotably mounted to support plate 172 via a pair of lever arms 188 and 189 (see FIG. 7). Lever arms 188 and 189 are rigid with an arm member 190 of a drive linkage 192 also comprising an actuator cylinder 194 having a plunger 196 pivotably connected at its free end to arm member 190.

Upon a rotation of carousel 20 so that transfer mechanism 18 is aligned with shaft 26, as illustrated in FIG. 6, control unit 34 shifts carousel 20 and thus transfer mechanism 18 towards shaft 26 so that outer wall 44 of vial 24 surrounds umbilical cord 12 coiled upon shaft 26 and so that finger 180 is inserted into shaft 26, as indicated in dot-dash lines in FIG. 6. Upon the attainment of the dot-dash position by vial 24, control unit 34 actuates cylinder 194 to pivot lever arms 188 and 189 so that retainer plate 186 covers the mouth of vial 24. To that end, retainer plate 186 is provided with a slot 187 (FIG. 7) having a width slightly larger that the diameter of shaft 26.

Upon a pivoting of retainer plate 186 to cover the mouth of vial 24, control unit 34 shifts carousel 20 and transfer mechanism 18 away from shaft 26, i.e., to the left in FIG. 6. During this shifting operation, retainer plate 186 engages the wound umbilical cord 12 and slides it off of shaft 26. Support plate 172 is then swung into a horizontal orientation and lever arms 188 and 189 pivoted to remove retainer plate from the mouth of vial 24. Cap 58 is then screwed onto vial 24, as described hereinafter with reference to FIG. 7.

As illustrated in FIG. 7, cleaning unit 14, aspirating unit 16 and transfer mechanism 18 are all mounted to a T-shaped frame 200 which is pivotably mounted to a main frame 202. For purposes of simplifying the drawing, aspirating unit 16 is only partially shown, motors 144 and 160 being omitted.

T-shaped frame 200 pivots about a vertical axis 204 with respect to main frame 202 by means of a motor unit 206 which receives enabling signals from control unit 34.

The umbilical cord support assembly comprising shaft 26, motor 70, hood 78 and funnel 100 is fixed to a frame plate 208 which is slidably mounted to a pair of cross-sectionally triangular rails 210 and 212 secured to main frame 202. Frame plate 208 and the umbilical cord support assembly carried thereon are reciprocated along rails 210 and 212 alternately towards and away from T-shaped frame 200 under the action of a motor 214 mounted to main frame 202 and connected to frame plate 208 via a worm shaft 216.

Pivotably mounted to a corner of main frame 202 for independent limited rotary motion about a vertical axis 218 are two arms 220 and 222. Arm 220 serves to load a vial 24 onto finger 180 of transfer mechanism 18, while arm 222 serves to attach a cap 58 to a vial 24 on finger 180 upon the loading of an umbilical cord 12 into the vial and upon a return of transfer mechanism 18 from the operative position in alignment with shaft 26 to a vial closure position. The structure and function of arms 220 and 222 are described in detail below with respect to FIGS. 7 and 8.

In the operation of the system of FIG. 7, T-shaped frame begins in the illustrated position, cup-shaped cleaning device 28 being aligned with shaft 26. Shaft 26, together with drive motor 70, hood 78 and funnel 100, is initially disposed at the far end of main frame 202. Upon the manual winding of an umbilical cord 12 about shaft 26 as described hereinabove, control unit 34 is signaled by an operator, e.g., via a non-illustrated switch, to begin operations. Control unit 34 then activates motor 214 to shift the umbilical cord 12 support assembly towards T-shaped frame 200 so that shaft 26 and the umbilical cord 12 wound thereon are inserted into cup-shaped cleaning device 28. As described above, motor 70 and cleaning unit 14 are then activated to clean the umbilical cord.

Upon the termination of the washing operation, control unit 34 activates motor 214 in reverse to move shaft 26 and umbilical cord 12 wound thereon out of cup-shaped cleaning device 28 towards the left hand side of frame 202, as shown in FIG. 7. Control unit 34 then energizes motor unit 206 to pivot T-shaped frame 200 so that aspirating unit is in the operative position in alignment with shaft 26. In addition, motor 214 is also activated to shift shaft 26 and umbilical cord 12 back to towards T-shaped frame 202. As described in detail hereinabove with reference to FIGS. 4 and 5, control unit 34 sequences the operations of aspirating unit 16 to extract a predetermined amount of blood from a vein or artery 116 in umbilical cord 12. Upon the extraction of the blood and the upward shifting of tertiary frame 142, together with the loaded hypodermic-type syringe 136, control unit 34 energizes motor 214 to shift shaft 26 and umbilical cord 12 back to the waiting station at the right hand side of FIG. 7. Subsequently, control unit 34 energizes motor unit 206 to pivot T-shaped frame 200 about axis 204 so that transfer mechanism 18 is shifted into the operative position in alignment with shaft 26. Transfer mechanism 18 has already been loaded with a vial 24, as shown in FIG. 6, by a sequence of operations described hereinafter with reference to FIGS. 7 and 8.

Upon the positioning of transfer mechanism 18, control unit 34 again energizes motor 214 and shifts shaft 26 and umbilical cord 12 wound thereon towards T-shaped frame 200. It is to be noted that the amount that motor 214 translates the umbilical cord support assembly along rails 210 and 212 depends on the particular operation to be undertaken, i.e., on the particular device, whether cleaning unit 14, aspirating unit 16 or transfer mechanism 18, positioned at the aligned location by T-shaped frame 200.

Control unit 34 operates transfer mechanism 18 as described hereinabove to remove the wound umbilical cord 12 from shaft 26, the sliding operation being effectuated by motor 214 pulling shaft 26 out of vial 24.

Upon the deposition of the wound umbilical cord in vial 24, T-shaped frame 200 is turned by motor unit 206 so that the positions of cleaning unit 14, aspirating unit 16 and transfer mechanism 18 shown in FIG. 7 are assumed. Motor 128 of aspirating unit 16 is then energized by control unit 34 to pivot secondary frame 118 (see FIGS. 4 and 5) to a first station 224 at which the fluidic contents of hypodermic-type syringe 136 are ejected into an ampule 164 (FIG. 4). Subsequently, motor 128 is again energized to angularly shift secondary frame 118 from station 224 to a second station 226, at which the empty hypodermic-type syringe 136 is ejected as discussed hereinabove with reference to FIG. 4. Motor 128 is then energized in reverse to return secondary frame 118 to first station 224 at which another hypodermic-type syringe 136 is pressed into position between spring clips 138 and 140.

Figure 8:
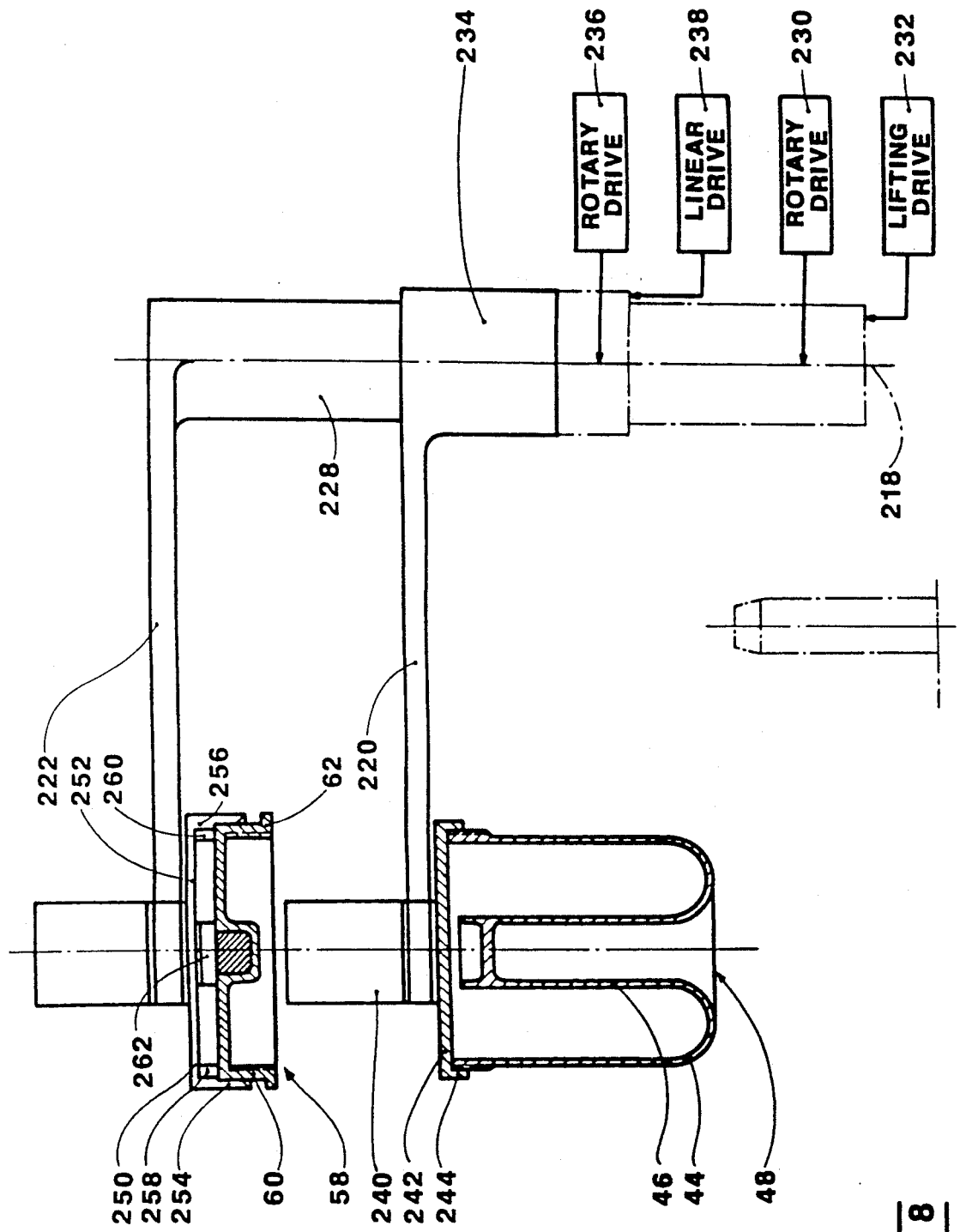
FIG. 8 is a side elevational view of a vial transfer and closure mechanism included in the system of FIG. 7.

As illustrated in FIGS. 7 and 8, arm 222 is connected to a cylindrical rod 228 pivotably and translatably mounted to main frame 202. Angular motion of rod 228 and arm 222 is effectuated by a rotary drive 230 under the control of control unit 34, while translatory motion is effectuated by a linear drive 232 also responsive to output signals of control unit 34.

Arm 220 is rigid with a collar 234 which is coaxial with rod 228. Collar 234 is pivoted about axis 218 under the action of a rotary drive 236 and is shiftable along axis 218 by a linear drive 238 both controlled by unit 34.

As further illustrated in FIGS. 7 and 8, arm 220 carried at a free end a rotary motor 240 actuated by control unit 34 and operatively connected to a lid-like element 242 for rotating that element about a vertical axis. Lid-like element is provided along an inner side of a shallow axially extending circumferential flange 244 with a thread for limitedly mating with the thread at the upper end of vial 24.

To load an empty vial 24 onto finger 180 of transfer mechanism 18, linear drive 238 moves collar 234 and arm 220 downwardly so that flange 244 engages the upper lip or rim of the empty vial at a loading station 246. Rotary motor 240 then rotates lid-like element 242 to temporarily secure the vial 24 to arm 220. Subsequently, linear drive 238 is energized in a reverse direction to raise arm 220 with entrained empty vial 24 and rotary drive 236 is energized to pivot arm 220 so that the empty vial carried by lid-like element 242 is positioned directly over finger 180. Linear drive 238 then deposits the empty vial onto finger 180, which is in a vertical orientation owing to the operation of pneumatic cylinder 173 (FIG. 6). Rotary motor 240 is activated to unscrew flange 244 of lid-like element 242 from the empty vial 24. To that end, it is necessary to key the vial to finger 180. Preferably, the outer cylindrical surface of finger 180 and the inner cylindrical surface of vial inner wall 46 are provided with interdigitating axially extending teeth (not shown) to prevent vial 24 from rotating with respect to lid-like element 242 during an unscrewing of lid-like element 242.

Upon the deposition of an empty vial 24 onto finger 180, support plate 172 is pivoted by pneumatic cylinder 173 (FIG. 6) under the control of unit 34 from the vertical orientation to the horizontal orientation, in preparation from a pivoting of T-shaped frame so that transfer mechanism 18 is aligned in the operative position with shaft 26. Lever arms 188 and 189 are positioned by actuator cylinder so that retainer plate 186 is in the retracted position shown in solid lines in FIG. 6.

Upon the completion of an umbilical cord loading operation and the subsequent pivoting of T-shaped frame 200 so that transfer mechanism 18 occupies the position shown in FIG. 7, pneumatic cylinder 173 (FIG. 6) is actuated by control unit 34 to pivot support plate 172 from a vertical orientation to a horizontal orientation. Actuator cylinder 194 is subsequently operated to pivot shift lever arms 188 and 189 so that retainer plate 186 is retracted from the mouth of vial 24. Control unit 34 then activates rotary 230 to shift arm 222 so that a cap 58 carried at the free end thereof is positioned over the open mouth of the vial 24 holding a coiled umbilical cord 12.

As shown in FIGS. 7 and 8, arm 222 is provided at a free end with a motor 248 having a rotor (not shown) secured to a pair of bars 250 and 252. Bars 250 and 252 carry at their radially outer ends respective axially extending arcuate plate elements 254 and 256 which are formed on their inner sides with longitudinally extending splines or teeth 258 and 260. Teeth 258 and 260 mesh with axially extending teeth or grooves (not separately designated) on an outer surface of cap flange 60. An electromagnet 262 is attached to arm 222 at the free end thereof below motor 248. Electromagnet 262 is energized by control unit 34 to hold cap 58 and, subsequently, also vial 24 during transfer operations.

Cap 58 is picked up by arm 222 at a cap loading station 264. In an action similar to the loading of an empty vial at station 246, rotary drive 230 and linear drive 232 are energized to move arm 222 into position at station 264. Upon the positioning of the free end of arm 222, electromagnet 262 is energized to magnetize metallic element 68 in cap 58, to thereby hold the cap to arm 222. Upon subsequent motion of arm 222 to bring the cap 58 directly over and in contact with the cord-carrying vial 24 on finger 18 of transfer mechanism 18, motor 248 is energized to rotate arms 250 and 252 and the cap 58 entrained thereto, thereby screwing the cap onto the vial. Upon completion the cap attachment operation, linear drive 232 and rotary drive 230 are activated by control unit 34 to transfer the vial and the cap to a transfer station 266 (FIG. 7) where electromagnet 262 is deenergized to release the vial and the cap screwed thereto onto a conveyor belt (not illustrated) or other mechanism for transporting the capped vial away from the system of FIG. 7.

As schematically depicted in FIG. 9, an assembly for placing a new hypodermic-type syringe 136 (FIGS. 4 and 5) between spring clips 138 and 140 on tertiary frame 142 comprises a trolley car 268 which is shifted by a linear drive 270 between a syringe loading station 272 and station 224 (FIG. 7), where a hypodermic-type syringe 136 is pressed into spring clips 138 and 140. Trolley car 268 carries a robot arm mechanism 274 including a first arm 276 pivoted about a first joint 278 by a first rotary drive 280 and a second arm 282 pivoted about a second joint 284 with respect to the first arm 276 by a second rotary drive 286. Joint 278 is supported on trolley car 268 via a pneumatic or hydraulic cylinder 287, while the free end of arm 282 carries a gripping element 288, for example, a pair of jaws or a spring clip exerting a clamping force less than the clamping force exerted by clips 138 and 140.

During a syringe loading operation, gripping element 288 is positioned over a lowermost hypodermic-type syringe 290 in a stack of empty syringes 292 held in a magazine or rack 294. Upon a grasping of syringe 290 by gripping element 288, cylinder 287 is actuated to raise the syringe and gripping element 288. Then rotary drives 286 and 280 are sequentially activated to bring syringe 290 in parallel and in horizontal alignment with spring clips 138 and 140, as indicated at 296. Linear drive 270 is then energized to shift trolley car 268 to press the syringe 290 into position between clips 138 and 140. Upon loading of the empty syringe onto tertiary frame 142, linear drive 270 is reversed to shift trolley car 268 away from station 224.

Prior to inserting an umbilical cord between shaft 26 and clamp 72, the ends of the cord are closed off to prevent fluid from leaking out of the cord. Preferably, the ends of the cord are clamped with plastic or metal bands such as staples 71 (FIG. 5). At least one of the bands as well as the vital 24, is marked with an identification code including identification of an individual to which said umbilical cord was attached in utero. The identification code may be applied in any known manner to the bands, for example, by embossing, laser writing, etching, or ink. The identification code may be applied before or after the band or tag is affixed to the umbilical cord. The information in the identification code includes in some cases information as to intended use of said umbilical cord, for example, whether the cord is intended in whole or in part for research, medical identification or therapeutic treatment.

It is to be noted that an anticoagulant is advantageously injected into an umbilical cord prior to winding thereof onto shaft 26. Alternatively, the anticoagulant may be injected using a hypodermic-type syringe 136 previously loaded with the anticoagulant. The injection operation may be accomplished automatically by the same apparatus as described herein. Essentially the only alteration in the aspirating unit 16 (FIGS. 4, 5 and 7) necessary to effectuate the automatic injection of an anticoagulant would be a modification of the programming of control unit 34. Such a modification is deemed well within the skill of those in the art. Other alterations of the aspirating unit 16 will also be readily apprehended by the skilled in the art.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An apparatus for removing a sample of fluid from an umbilical cord having an external membrane, comprising:
   holding means supporting an umbilical cord in a coiled configuration; and
   aspirating means for puncturing a membrane of said umbilical cord and aspirating a quantity of fluid from said umbilical cord while said umbilical cord is supported in said coiled configuration by said holding means.

2. The apparatus recited in claim 1, further comprising:
   detecting means for detecting a location of fluid within said umbilical cord;
   carriage means for moving one of said holding means and said aspirating means relative to the other; and
   control means operatively connected to said detection means and said carriage means for controlling the motion of said holding means and said aspirating means relative to one another, said control means being operatively connected to said aspirating means for triggering the operation thereof upon an attainment of a desired relative position of said holding means and aspirating means.

3. The apparatus recited in claim 2 wherein said holding means includes:
   a shaft;
   support means for supporting said shaft in a predetermined orientation; and
   means for releasably holding the umbilical cord in a coiled configuration about said shaft.

4. The apparatus recited in claim 3 wherein said shaft is at least partially hollow and said detection means includes a light source and photodetector means for sensing a vein or artery of said umbilical cord, said detection means further including drive means for shifting said light source into said shaft.

5. The apparatus recited in claim 4 wherein said detection means further includes means for rotating said photodetector means in an arc about a coil of the umbilical cord.

6. The apparatus recited in claim 2 wherein said detection means includes a light source and photodetector means for sensing a vein or artery of said umbilical cord.

7. The apparatus recited in claim 6 wherein said detection means further includes means for moving said photodetector means along a predetermined path relative to the umbilical cord.

* * * * *